US00PP09711P

United States Patent [19]

Danziger

[11] Patent Number: Plant 9,711

[45] Date of Patent: Nov. 26, 1996

[54] *GYPSOPHILA PANICULATA* NAMED 'DANGHAPPY'

[75] Inventor: Gabriel Danziger, Nir Tzvi, Israel

[73] Assignee: Danziger "Dan" Flower Farm, Post Beit Dagan, Israel

[21] Appl. No.: 513,525

[22] Filed: Aug. 10, 1995

[51] Int. Cl.[6] ..... A01H 5/00

[52] U.S. Cl. ..... Plt./68.1

[58] Field of Search ..... Plt./68.1

*Primary Examiner*—James R. Feyrer
*Attorney, Agent, or Firm*—Foley & Lardner

[57] ABSTRACT

A new cultivar of Gypsophila named Danghappy, characterized by its compact growth habit, ability to flower in periods of relatively lower light, good yield, and its floriferous habit.

1 Drawing Sheet

The present invention relates to a new and distinct cultivar of Gypsophila plant botanically known as Gypsophila, and known by the cultivar name Danghappy.

The new cultivar was developed by the inventor Gabriel Danziger through controlled breeding conducted in Mostav Mishmar Hashiva, Israel by crossing male and female parents which are unknown at this time. Both parents are proprietary cultivar used in the breeding program.

Asexual reproduction by terminal or stem cuttings taken at Moshav Mishmar Hashiva, Israel by the inventor has shown that the unique features of this new cultivar are stabilized and are reproduced true to type in successive propagations.

The following characteristics distinguish the new cultivar from both its parent cultivars and other cultivated Gypsophila of this type known and used in the floriculture industry:

1. Compact habit of growth. When in full flower, Danghappy has a height of approximately 30 cm, compared to a height of 50 cm for the well known cultivar White Festival, discussed in U.S. Plant Pat. No. 8,652.

2. Danghappy is responsive to relatively lower periods of light for flowering. As a result, Danghappy will flower earlier in the spring and later in the autumn. Danghappy is similar in this respect to White Festival and requires substantially less light for flowering than other cultivars such as Perfecta.

3. The new cultivar has a good yield.

The accompanying colored photograph illustrates the overall appearance of this cultivar, showing colors as true as it is reasonably possible to obtain in a colored reproduction of this type.

The following is a detailed description of Danghappy based on plants produced under commercial practice and conditions, in a Plastic covered greenhouse in Israel with maximum day temperatures of 25° C. and minimum night temperatures of 16° C.

Color references are made to The Royal Horticultural Society Colour Chart (R.H.S.), except where general terms of ordinary dictionary significance are used.

Parentage: The parents of Danghappy are seedlings which are not known at this time.

Propagation:

*Type cutting.*—Leaf cuttings.

*Time to initiate roots.*—10 days at 25° C. summer, and 15 days at 20° C. winter.

*Rooting habit.*—Good.

Plant description:

*Form.*—Generally upright but spreading, excellent for bedding and flowering pots.

*Habit of growth.*—Compact (30 cm), with very good branching.

*Foliage description.*—Size: Approximately 6 mm wide and 50 mm long. Shape: Elongated, slightly transversed, convex, with pointed tip. Margin: Entire. Color: Green with a red midvein. Young foliage: Top side, 147A; under side, 147B. Mature foliage: Top side, 147A; under side, 147B. Venation: None.

Flowering description:

*Flowering habit.*—Flower is approximately 5–6 weeks in the summer.

*Natural flowering season.*—From spring to fall.

*Flower buds.*—Small and round, turning white after opening.

*Flowers borne.*—On rigid pedicels, 10–12 days from closed but to open flower.

*Quantity of flowers.*—Very floriferous.

*Petals.*—Shape: Generally round to oblong. Color: White. Top side: White, 155D with very light green center, with very little fading. When temperature are relatively, color turns to very pale pink. Under side: White. Number of petals: 20. Size of flowers: 9–10 MM. in diameter.

*Reproductive organs.*—Stamens: Five (5) in number. Anther shape: Stringy. Anther color: White. Pollen color: White. Pistels: Stigma shape: Conical. Stigma color: White. Style color: White. Ovaries: (Five) 5 in number, 1.2 mm long, light green in color.

Resistance to disease: To date, the new cultivar has not shown any abnormal susceptibility to disease.

It is claimed:

1. A new and distinct cultivar of Gypsophila named Danghappy, as illustrated and described.

* * * * *

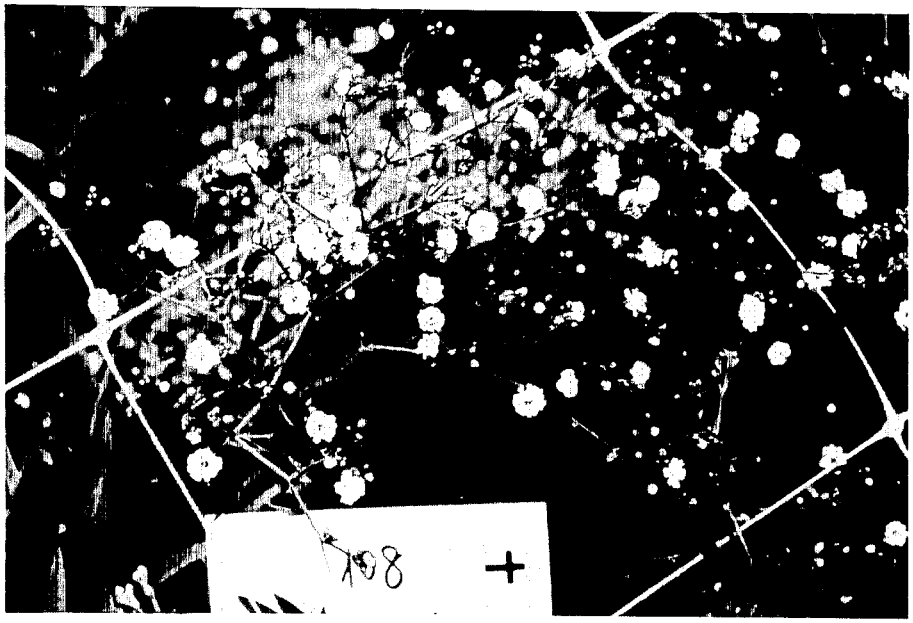
108

UNITED STATES PATENT AND TRADEMARK OFFICE

CERTIFICATE OF CORRECTION

PATENT NO. : PP 9,711
DATED : November 26, 1996
INVENTOR(S) : Gabriel Danziger

It is certified that error appears in the above-identified patent and that said Letters Patent is hereby corrected as shown below:

Title page, Item [54] and Column 1, line 3,
Title, please delete "DANGHAPPY" and replace it with -- DANGYHAPPY --.

Title page,
Item [57], ABSTRACT,
Line 1, please delete "Danghappy" and replace it with -- Dangyhappy --.

Column 1,
Line 5, please delete "Mostav" and replace it with -- Moshav --.
Lines 17, 21, 22, 23, 32 and 40, please delete "Danghappy" and replace it with -- Dangyhappy --.

Column 2,
Line 40, please delete "Danghappy" and replace it with -- Dangyhappy --.

Signed and Sealed this

Eleventh Day of October, 2005

JON W. DUDAS
*Director of the United States Patent and Trademark Office*

UNITED STATES PATENT AND TRADEMARK OFFICE

CERTIFICATE OF CORRECTION

PATENT NO. : PP 09,711
APPLICATION NO. : 08/513525
DATED : November 26, 1996
INVENTOR(S) : Gabriel Danziger It is certified that error appears in the above-identified patent and that said Letters Patent is hereby corrected as shown below:

Item [54], Title:

Please delete [‘DANGHAPPY’] and replace it with ‘DANGYHAPPY’.

Item [57], Abstract:

Ln 1

Please delete [Danghappy] and replace it with Dangyhappy.

Column 1,

Line 3, please delete [Danghappy] and replace it with Dangyhappy.

Column 1,

Line 5, please delete [Mostav] and replace it with Moshav.

Column 1,

Line 17, please delete [Danghappy] and replace it with Dangyhappy.

Column 1,

Lines 21, 22 & 23, please delete [Danghappy] and replace it with Dangyhappy.

Column 1,

Line 32, please delete [Danghappy] and replace it with Dangyhappy.

Column 1,

Line 40, please delete [Danghappy] and replace it with Dangyhappy.

.

UNITED STATES PATENT AND TRADEMARK OFFICE

CERTIFICATE OF CORRECTION

PATENT NO. : PP09,711
APPLICATION NO. : 08/513525
DATED : November 26, 1996
INVENTOR(S) : Gabriel Danziger It is certified that error appears in the above-identified patent and that said Letters Patent is hereby corrected as shown below:

Column 2,

Line 40, please delete [Danghappy] and replace it with Dangyhappy.

Signed and Sealed this

Twenty-second Day of August, 2006

JON W. DUDAS
*Director of the United States Patent and Trademark Office*